United States Patent
LeGrow et al.

(10) Patent No.: US 6,770,123 B2
(45) Date of Patent: Aug. 3, 2004

(54) PROTECTIVE COATINGS HAVING BRANCHED TRIMETHYLSILYLATED ALKYLSILSESQUIOXANE EMULSIONS

(75) Inventors: Gary E. LeGrow, Newberry, FL (US); W. Leonard Terry, Jr., Gainesville, FL (US)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/201,173

(22) Filed: Jul. 23, 2002

(65) Prior Publication Data

US 2004/0016364 A1 Jan. 29, 2004

(51) Int. Cl.$^7$ .............................. C09D 5/02; C09K 3/18
(52) U.S. Cl. ................. 106/2; 106/287.13; 106/287.14; 427/387; 428/447
(58) Field of Search ............................... 106/2, 287.13, 106/287.14; 427/387; 428/447

(56) References Cited

U.S. PATENT DOCUMENTS

| | | | |
|---|---|---|---|
| 3,392,040 A | 7/1968 | Kass ........................ 106/287 |
| 3,395,028 A | 7/1968 | Mackles ..................... 106/8 |
| 3,956,174 A | 5/1976 | Palcher ................... 252/400 R |
| 4,133,921 A | 1/1979 | Palcher ..................... 427/355 |
| 4,462,828 A | 7/1984 | Otsuki ........................ 106/3 |
| 4,620,878 A | 11/1986 | Gee ..................... 106/287.15 |
| 4,631,273 A | 12/1986 | Blehm et al. ................ 514/29 |
| 4,640,792 A | 2/1987 | Groenhof et al. ........... 252/78.3 |
| 4,732,612 A | 3/1988 | Steer et al. .................. 106/10 |
| 4,810,407 A | 3/1989 | Sandvick ..................... 252/90 |
| 5,017,221 A | 5/1991 | Legrow et al. ................ 106/2 |
| 5,227,200 A | 7/1993 | LeGrow .................... 427/387 |
| 5,643,555 A * | 7/1997 | Collin et al. ................. 424/59 |
| 5,932,231 A | 8/1999 | LeGrow et al. ............ 424/401 |
| 6,489,274 B1 * | 12/2002 | LeGrow et al. ............ 510/122 |

FOREIGN PATENT DOCUMENTS

EP 001199343 A2 * 4/2002

* cited by examiner

*Primary Examiner*—Anthony J. Green
(74) *Attorney, Agent, or Firm*—Anthony A. Bisulca

(57) ABSTRACT

A protective coating for organic substrates includes an emulsion having a branched trimethylsilylated alkylsilsesquioxane. The trimethylsilylated alkylsilsesquioxane has the formula:

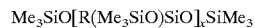

$$Me_3SiO[R(Me_3SiO)SiO]_xSiMe_3$$

wherein R is a substituted or unsubstituted linear or branched monovalent hydrocarbon substituent with from 6 to 14 carbon atoms, Me is Methyl, and x ranges from 1 to 6. Also disclosed is a method of rendering an organic surface repellent to water, dust and dirt by treating the organic surface with an effective amount of the foregoing emulsion. The organic surface being treated can be a rubber surface such as wires, cables, the sidewall of automotive tires, footwear, and coated fabrics. The surface can also be a synthetic plastic surface such as automotive dashboards, automotive trim (both interior and exterior), automotive upholstery, flooring, residential siding, and piping.

20 Claims, No Drawings

PROTECTIVE COATINGS HAVING BRANCHED TRIMETHYLSILYLATED ALKYLSILSESQUIOXANE EMULSIONS

FIELD OF THE INVENTION

The present invention relates generally to silicone compositions, and in particular, to emulsions comprising a branched trimethylsilylated alkylsilsesquioxane.

BACKGROUND OF THE INVENTION

Aqueous emulsions of polydimethylsiloxane fluids have been applied to many surfaces as a protective coating. Such surfaces include for example, rubber, vinyl, plastic, and leather. Some of these surfaces are said to have been rendered anti-static for the purpose of repelling dust and dirt. When these emulsions are employed as protective coatings in outdoor applications, such as the sidewall of an automotive tire, the polydimethylsiloxane coating is rapidly removed by water which is encountered when the tire is exposed to rain or snow. In order to restore the protective coating to the tire, another application of the polydimethylsiloxane emulsion is required. This is time consuming and a repeated expense, and thus, reduces consumer acceptance. Exemplary of such polydimethylsiloxane emulsion coatings are U.S. Pat. No. 3,956,174, issued May 11, 1976 and U.S. Pat. No. 4,133,921, issued Jan. 9, 1979.

Recognizing the deficiencies of polydimethylsiloxane fluids, aqueous emulsions of linear polymethylalkylsiloxanes are disclosed in U.S. Pat. No. 5,017,221, issued May 21, 1991. U.S. Pat. No. 5,017,221 states that coatings on organic substrates produced from these emulsions, when exposed to rain and snow in outdoor applications, were less readily removed from the substrate than polydimethylsiloxane coatings. The alleged increased efficacy of the coatings derived from the linear polymethylalkylsiloxane emulsions was believed to be due to the presence of the alkyl groups which have a strong affinity for organic surfaces including rubber and plastics. Coatings derived from polymethylalkylsiloxanes, however, are also believed to be susceptible to degradation or removal from the substrate upon exposure to inclement weather. The inability of these polymethylalkylsiloxane coatings to resist inclement weather is likely attributable to the fact that such compounds are generally linear, and in consequence, such coatings tend to lay on the surface of the substrate to which they are applied, rather than be absorbed by the interstices within the substrate. Additionally, polymethylalkylsiloxanes coatings, as stated in U.S. Pat. No. 5,017,221, produce a glossy, lusterous appearance, which in turn deleteriously affects consumer acceptance when the coating is to be applied to certain substrates, such as, for example, automobile tires.

A need therefore exists for a compound capable of forming an aqueous emulsion to be used in protective coatings which exhibits prolonged adherence to a substrate, and produces a non-glossy or matte appearance.

SUMMARY OF THE INVENTION

The present invention is directed to an emulsion, and a protective coating, which includes a branched trimethylsilylated alkylsilsesquioxane with the formula:

wherein R is a substituted or unsubstituted linear or branched monovalent hydrocarbon substituent with from 6 to 14 carbon atoms, Me is Methyl, and x ranges from 1 to 6.

According to another aspect of the invention, a method of rendering an organic surface repellent to fluids and particulates includes treating the substrate with an emulsion having a branched trimethylsilylated alkylsilsesquioxane.

The protective coating formed with the trimethylsilylated alkylsilsesquioxane exhibits superior resistance to degradation caused by inclement weather and thus minimizes the need for repeated applications, while providing a matte appearance which is aesthetically appealing to consumers.

These and other objects, advantages, purposes and features of the invention will become apparent upon review of the following detailed description.

DETAILED DESCRIPTION OF THE PREFERRED EMBODIMENTS

The present invention relates to a protective coating for treating organic substrates which renders the same repellant to fluids and particulate matter, such as, for example, water, snow, road salt, dirt, debris, etc., The protective coating includes a branched, non-linear, trimethylsilylated alkylsilsesquioxane. In a preferred form, the protective coating is in the form of an emulsion.

The protective coating of the present invention may be used to treat a wide variety of organic substrates. Non-limiting examples of organic substrates include rubber substrates such as wires, cables, the sidewall of automotive tires, footwear, and coated fabrics; and synthetic plastic substrates such as automotive dashboards, automotive trim (both interior and exterior), automotive upholstery, flooring, residential siding, and piping.

The branched trimethylsilylated alkylsilsesquioxane has the following branched, non-linear structure:

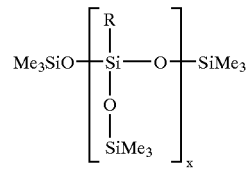

wherein R is a substituted or unsubstituted linear or branched monovalent hydrocarbon substituent with from 6 to 14 carbon atoms, Me is Methyl, and x ranges from 1 to 6. For example, R, having from 6 to 14 carbon atoms, may be hexyl, n-hexyl, 2-(perfluorobutyl)ethyl, heptyl, octyl, n-octyl, 1-(perfluorohexyl)ethyl, nonyl, decyl, dodecyl, tetradecyl and the like, or may comprise any other monovalent hydrocarbon substituent known to those of ordinary skill in the art. Additionally, it is contemplated herein that each R may be the same or different monovalent hydrocarbon substituent. The value of x in the above formula for the trimethylsilylated alklysilsesquioxane for the most preferred embodiment ranges from 2 to about 6.

Preferably, the branched trimethylsilylated alkylsilsesquioxane is a fluid and has a high purity which is substantially free of polydimethylsiloxanes, organic and inorganic chemicals. The synthesis of the high purity branched trimethylsilylated alkylsilsesquioxane fluid is disclosed in U.S. Pat. No. 5,932,231, issued Aug. 3, 1999, the entire disclosure of which is hereby incorporated herein by reference. The high purity branched trimethylsilylated alkylsilsesquioxane fluid has a viscosity in the range from about 20 centistoke to about 1000 centistoke, measured at 25 degrees Centigrade, preferably 200 to 500 centistoke, with a viscosity between 300 and 400 centistoke being the most preferred. As stated hereinabove, the protective coating is preferably in the form of an emulsion comprising the branched trimethylsilylated alkylsilsesquioxane fluid, a continuous phase, or carrier liquid, and a surfactant. The carrier liquid may be mineral oil, vegetable oil, polydimethyl silicones, cyclic siloxanes, water, methylsiloxanes having a viscosity of less than about ten centistokes including, but not limited to cyclopolysiloxanes of the formula $[(CH_3)_2SiO]_x$ and linear siloxanes of the formula $(CH_3)_3SiO[(CH_3)_2Si]_xSi(CH_3)_3$ in which x is an integer having a value of from three to ten and y is an integer having a value of from zero to about four; hydrocarbons having from about six to sixteen carbon atoms including straight and branched chains. Preferably, the carrier liquid is water. The surfactant can be cationic, anionic, non-ionic, silicone-modified, silicone copolyols or mixtures thereof. The concentration of carrier liquid should be sufficient to enable the emulsion to be readily dispensed from a typical household container with or without the aid of an adjustable spray head. In a preferred form, the emulsion also includes a polyglycol, non-limiting examples of which include ethylene glycol, propylene glycol, butylene glycol, mixtures thereof, and copolymers thereof. The polyglycol reduces the surface tension of the water with respect to the substrate and thereby improves the spreading of the continuous phase of the emulsion.

The branched trimethylsilylated alkylsilsesquioxane is present in an amount between approximately 5% and 35% by weight, preferably between approximately 15% and 25%. The carrier liquid used is between approximately 65% and 95%, preferably 75% and 85%; while the surfactant concentration is between approximately 1% and 5%; preferably between approximately 2% and 3%. If a polyglycol is employed, it is present in an amount between approximately 0.1% and 1.0%, preferably between 0.2% and 0.6%. The emulsion can be made in accordance with any emulsion technique commonly employed by those with ordinary skill in the art.

While not wishing to be bound by theory, the enhanced functional benefits of the protective coatings of the present invention are believed to be attributable to the greater ability of the branched trimethylsilylated alkylsilsesquioxane fluids to spread on the organic surface of the substrate and to penetrate said surface. That is, the branched, three dimensional structure of the trimethylsilylated alkylsilsesquioxane fluids is believed to enable the compound to be absorbed by the interstitial spaces present in the organic substrate to which it is applied. The trimethylsiloxy group content of the branched trimethylsilylated alkylsilsesquioxane fluids is far greater than that present in either polydimethylsiloxane or linear polyalkylmethylsiloxane fluids of similar viscosity. Table I shows the calculated % trimethylsiloxy content of the three types of polymers.

TABLE I

CALCULATED TRIMETHYLSILOXY GROUP
CONTENT OF 350 cs SILICONES

| SILICONE POLYMER TYPE | FORMULA | % Me3SiO |
|---|---|---|
| Polydimethylsiloxane | Me3SiO(Me2SiO)xSiMe3 | 1.2 |
| Polyalkylmethylsiloxane | Me3SiO(n-HexylMeSiO)35SiMe3 | 3.1 |
| Trimethylsilylated Alkylsilsesquioxane | Me3SiO(n-Octyl(Me3SiO)SiO)x-SiMe3 | 19.7 |

In addition, the molecular weight of the branched trimethylsilylated alkylsilsesquioxanes of 350 cs viscosity is significantly lower than the molecular weights of polydimethylsiloxane or linear polyalkylmethylsiloxanes of the same viscosity. Thus, the smaller, largely spherical molecules of the branched trimethylsilylated alkylsilsesquioxanes are able to spread on organic substrates and penetrate the substrate's pores better than the other types of silicones and then, because of their high alkyl content, are held there more tenaciously. Another significant difference between the protective coatings formed of trimethylsilylated octylsilsesquioxane and commercially available tire treatments containing polydimethylsiloxanes is the fact that the coatings according to the present invention are not shiny; rather, they have a matte appearance within a few hours of being applied. This matte appearance does not change with time.

The following examples illustrate the present invention. They are not to be construed to limit the scope of the appended claims in any manner whatsoever.

EXAMPLES

In the following examples, Tergitol® TMN-6 is a trademark of Union Carbide Corporation and is polyethylene glycol trimethylnonyl ether (CAS# 60828-78-6). Triton® W-30 is a trademark of Union Carbide Corporation and is sodium alkyl aryl ether sulfate (CAS# 55348-40-8). Westley's® Bleche-White Tire Cleaner is a trademark of Blue Coral, Inc.

Example 1

From an addition funnel, a mixture of 495 g (2.0 mole) of octyltrichlorosilane and 108.5 g (1.0 mole) of trimethylchlorosilane was slowly added, with vigorous stirring, to 3 liter 3 necked round bottom flask equipped with a mechanical stirrer, water condenser, heating mantle, thermometer and nitrogen overgas containing 1195 g (66.4 mole) of distilled water. The rate of addition was controlled to limit the reaction temperature to 60 C. After the addition was complete, the contents of the flask were heated for an additional hour at 60 C and then allowed to cool to 40 C. The lower acidic aqueous layer was removed from the flask and replaced by 400 g of hexamethyldisiloxane and 500 g of distilled water. This mixture was stirred at 40 C for ½ hour and then allowed to settle, followed by removal of the lower acidic aqueous layer. The silicone layer was washed with a further 500 g of water as above and after allowing the mixture to separate the lower acidic aqueous layer was removed. The silicone layer was heated to reflux and water was azeoptroped out of the mixture until it was clear. One gram of trifluoromethanesulfonic acid was added to the flask and the mixture was heated and stirred at 100 C for 1 hour. The mixture was cooled to room temperature and 50 g of anhydrous calcium carbonate was added and stirred for 1 hour. The suspension was then filtered to remove the calcium carbonate and the trifluoromethanesulfonic acid. Hexamethyldisiloxane was stripped from the product under vacuum at 50 C leaving 395 g of clear, colorless and odorless trimethylsilylated octylsilsesquioxane fluid with a Refractive Index at 25 C of 1.44, specific gravity at 25 C of 0.89 and viscosity at 25 C of ~350 cs.

Example 2

A mixture of 18.33 g of distilled water, 6.34 g of Tergitol® TMN-6 surfactant, and 1.43 g of Triton® W-30 surfactant was prepared with a Tissue-Tearor Homogenizer running at approximately 6000 rpm. To this mixture was slowly added with stirring at approximately 6000 rpm 100 g of Trimethylsilylated octylsilsesquioxane fluid produced in Example 1. After the addition was complete, a solution of 0.38 g of sodium bicarbonate, 0.46 g of ethylene glycol and 36.72 g of distilled water was slowly added with stirring at 6000 rpm. The emulsion was then diluted with 236.4 g of distilled water to produce 400 g of final emulsion. The emulsion was assayed by heating a 2 g sample in an aluminum dish in an air circulating oven at 100 C for 1 hour. The % non-volatile residue was determined to be 25.0+/−1.0.

Example 3

A mixture of 158 g of Tergitol® TMN-6, 36 g of Triton® W-30 and 459 g of distilled water was prepared in a 22 liter vessel. To this mixture was added 2500 g of Trimethylsilylated octylsilsesquioxane fluid produced in Example 1 using an IKA R-1331 anchor stirrer. When the addition was complete, a solution of 9.5 g of sodium bicarbonate, 10.8 g of ethylene glycol and 916 g of distilled water was added using the IKA R-1331 stirrer. The emulsion was then diluted with 5910 g of distilled water using an IKA T25 in-line homogenizer, recirculating the emulsion to the vessel. The T25 homogenizer was run for ½ hour after the addition was complete to insure the emulsification was complete. The final emulsion weighed 9968 g and was assayed by the method described in Example 2. The % non-volatile residue was 25.3+/−1.0.

Example 4

The side walls of the front and rear right side tires of 4 vehicles (a 1990 GMC Van, 1991 Ford Ranger, a 1996 Ford Ranger, and a 2000 Plymouth Mini-Van) were scrubbed with Westley's Bleche-White Tire Cleaner, rinsed with fresh water and then allowed to dry. The emulsion from Example 3 was then sprayed on the side walls of the front and rear right side tires only of all four vehicles. The emulsion was spread on the rubber surfaces to achieve a uniform coating with a cloth and to remove any excess. The coatings were allowed to dry several hours before the vehicles were moved. Subsequent to the application of these coatings the tires on both sides of the car were inspected monthly for 6 months by spraying them with a garden hose. The treated tire walls were not wetted by water and any dust on the tire walls washed off readily leaving a clean dry water repellent surface almost immediately. The untreated tire walls, particularly those on vehicles which regularly travel on clay roads, did not readily shed clay dust when sprayed with water. In addition they were readily wetted, and took a considerable amount of time to dry off, often showing residual soil marks.

It is to be understood that the foregoing is a description of the preferred embodiments. Those skilled in the art will recognize that variations, modifications and improvements may be made without departing from the spirit and scope of the invention disclosed herein. The scope of protection afforded the present invention is to be measured by the claims which follow in the breadth of interpretation which the law allows.

What is claimed is:

1. A protective coating composition for protecting a substrate from dust, dirt, particulate matter and/or inclement weather comprising an emulsion including a branched trimethylsilylated alkylsilsesquioxane having the formula:

$$Me_3SiO[R(Me_3SiO)SiO]_xSiMe_3$$

wherein R is a substituted or unsubstituted linear or branched monovalent hydrocarbon substituent with from 6 to 14 carbon atoms, Me is Methyl, and x ranges from 1 to 6, wherein the substrate is selected from the group consisting of wires, cables, the sidewalls of automotive tires, footwear, coated fabrics; synthetic plastic substrates, automotive dashboards, automotive trim (both interior and exterior), automotive upholstery, flooring, residential siding, and piping.

2. The protective coating composition of claim 1, further comprising a carrier liquid.

3. The protective coating composition of claim 2, wherein said carrier liquid is water.

4. The protective coating composition of claim 1, further comprising at least one surfactant.

5. The protective coating composition of claim 1, further comprising a polyglycol.

6. The protective coating composition of claim 5, wherein said polyglycol is selected from the group consisting of ethylene glycol, propylene glycol, butylene glycol, mixtures thereof, and copolymers thereof.

7. An emulsion comprising a branched trimethylsilylated alkylsilsesquioxane having the formula:

$$Me_3SiO[R(Me_3SiO)SiO]_xSiMe_3$$

wherein R is a substituted or unsubstituted linear or branched monovalent hydrocarbon substituent with from 6 to 14 carbon atoms, Me is Methyl, and x ranges from 1 to 6, wherein said branched trimethylsilylated alkylsilsesquioxane has a viscosity in the range of from about 20 centistokes to about 1000 centistokes, measured at 25 C.

8. An emulsion comprising a branched trimethylsilylated alkylsilsesquioxane having the formula:

$$Me_3SiO[R(Me_3SiO)SiO]_xSiMe_3$$

wherein R is a substituted or unsubstituted linear or branched monovalent hydrocarbon substituent with from 6 to 14 carbon atoms, Me is Methyl, and x ranges from 1 to 6 wherein said branched trimethylsilylated alkylsilsesquioxane has a viscosity in the range of from about 200 centistokes to about 500 centistokes, measured at 25 C.

9. The protective coating composition of claim 1, wherein said branched trimethylsilylated alkylsilsesquioxane is trimethylsiloxy octylsilsesquioxane.

10. A method of rendering an organic substrate repellent to fluids and particulates comprising the step of treating the substrate with an emulsion including a branched trimethylsilylated alkylsilsesquioxane having the formula:

$$Me_3SiO[R(Me_3SiO)SiO]_xSiMe_3$$

wherein R is a substituted or unsubstituted linear or branched monovalent hydrocarbon substituent with from 6 to 14 carbon atoms, Me is Methyl, and x ranges from 1 to 6.

11. The method of claim 10, wherein said branched trimethylsilylated alkylsilsesquioxane has a viscosity in the range of from about 20 centistokes to about 1000 centistokes, measured at 25 C.

12. The method of claim 10, wherein said branched trimethylsilylated alkylsilsesquioxane has a viscosity in the range of from about 200 centistokes to about 500 centistokes measured at 25 C.

13. The method of claim 10, wherein said branched trimethylsilylated alkylsilsesquioxane is trimethylsiloxy octylsilsesquioxane.

14. The method of claim 10, wherein said organic substrate is selected from the group consisting of wires, cables, the sidewall of automotive tires, footwear, and coated fabrics, automotive dashboards, interior automotive trim, exterior automotive trim, automotive upholstery, flooring, residential siding, and piping.

15. The method of claim 10, further comprising water.

16. The method of claim 10, further comprising at least one surfactant.

17. The method of claim 10, further comprising a polyglycol.

18. The method of claim 17, wherein said polyglycol is selected from the group consisting of ethylene glycol, propylene glycol, butylene glycol, mixtures thereof, and copolymers thereof.

19. An automotive parts protective coating composition for protecting an automotive substrate from dust, dirt, particulate matter, and/or inclement weather comprising a branched trimethylsilylated alkylsilsesquioxane having the formula:

$$Me_3SiO[R(Me_3SiO)SiO]_xSiMe_3$$

wherein R is a substituted or unsubstituted linear or branched monovalent hydrocarbon substituent with from 6 to 14 carbon atoms, Me is Methyl, and x ranges from 1 to 6.

20. The automotive parts protective coating composition of claim 19, wherein said branched trimethylsilylated alkylsilsesquioxane is trimethylsiloxy octylsilsesquioxane.

* * * * *